United States Patent [19]

Thornfeldt

[11] Patent Number: 5,057,500
[45] Date of Patent: Oct. 15, 1991

[54] TREATMENT OF PRURITIS WITH ESTERS AND AMIDES

[75] Inventor: Carl R. Thornfeldt, Ontario, Oreg.

[73] Assignee: Dermatologic Research Corporation, Napa, Calif.

[21] Appl. No.: 478,871

[22] Filed: Feb. 12, 1990

[51] Int. Cl.$^5$ .......................................... A61K 31/715
[52] U.S. Cl. ..................... 514/53; 514/546; 514/547; 514/552; 514/625; 514/627; 514/629
[58] Field of Search ................. 514/53, 546, 547, 552, 514/625, 627, 629

[56] References Cited

U.S. PATENT DOCUMENTS

| | | | |
|---|---|---|---|
| 3,535,422 | 10/1970 | Cox et al. | 424/164 |
| 3,670,080 | 6/1972 | Hirata | 514/172 |
| 3,953,591 | 4/1976 | Snyder | 424/80 |
| 4,067,997 | 1/1978 | Kabara | 424/312 |
| 4,343,798 | 8/1982 | Fawzi | 424/240 |
| 4,406,884 | 9/1983 | Fawzi et al. | 424/81 |
| 4,485,029 | 11/1984 | Kato et al. | 252/106 |
| 4,552,872 | 11/1985 | Cooper et al. | 514/175 |
| 4,746,515 | 5/1988 | Cheng et al. | 424/449 |
| 4,751,087 | 6/1988 | Wick | 424/449 |
| 4,764,379 | 8/1988 | Sanders et al. | 424/449 |
| 4,788,062 | 11/1988 | Gale et al. | 424/449 |
| 4,808,610 | 2/1989 | Munayyer et al. | 514/172 |
| 4,820,720 | 4/1989 | Sanders et al. | 514/356 |

FOREIGN PATENT DOCUMENTS 2912438 11/1988 Fed. Rep. of Germany.

OTHER PUBLICATIONS

Federal Register Part II, vol. 48, No. 27, Dept. of Health and Human Services Food and Drug Administration, External Analgesic Drug Products for Over-the Counter Human Use, Tuesday, Feb. 8, 1983, pp. 5867-5868.
Newcomer, V. D., Young E. M. eds., Geriatric Dermatology Igaku-Shoin, Tokyo, Japan, 1989, pp. 207-222.
Glantz et al., "an Antimicrobial System for the Oral Cavity Bases on an Aqueous Lipid Dispersion", J. Dispersion Science and Technology, 3(4), 373-378 (1982).

*Primary Examiner*—Leonard Schenkman
*Attorney, Agent, or Firm*—Townsend and Townsend

[57] ABSTRACT

This invention relates to a new topical pharmaceutical composition for the treatment of pruritis, especially psychogenic and senile types, that contains esters and amides of 5 to 19 carbon atom length monocarboxylic acids. These esters and amides are formulated alone or with other known topical antipruritic agents, such as amine and "Caine" anesthetics, alcohols, ketones, antihistamines, corticosteroids, counterirritants, and any combination of these.

13 Claims, No Drawings

TREATMENT OF PRURITIS WITH ESTERS AND AMIDES

BACKGROUND OF THE INVENTION

This invention relates to a topical treatment of systemic and localized pruritis, with particular interest as applied to psychogenic and senile pruritis.

Pruritis is a condition in which itching is the primary complaint and is unaccompanied by any visible causative lesion of the skin. Itching is perceived only in the skin, mucous membranes and cornea. The perception is localized to the dermoepidermal junction. No one receptor is uniquely adapted to itch perception.

There are many causes of localized or generalized pruritis. Many dermatoses have a predilection for certain areas of the body and can result in localized pruritis. Another cause of localized pruritis is notalgia paresthetica. Widespread itching or generalized pruritis is caused by a number of external factors and internal conditions. The most common group of causative factors are environmental provoking factors, including climate, particulate matter, detergents, insects, and infestations. The second most common group of causative factors includes a variety of skin diseases. The third most common group, yet most difficult to treat, includes psychogenic and senile pruritis. These last two are diagnoses of exclusion, yet they can be extremely debilitating and, since some cases are untreatable, can drive patients to suicide. Underlying systemic diseases account for 10% to 30% of generalized pruritis and are treated by reversing the underlying process.

When a patient begins scratching skin or mucous membranes that itch, no matter what the stimulation, a cycle to perpetuate the itch occurs. The cycle continues because of the cutaneous pleasure (orgasme cutane) one associates with scratching. Unless medical treatment interrupts this cycle, scratching continues until enough damage occurs that pleasure is replaced with pain.

Since no specific treatment is available and since no underlying etiology is elucidated in most patients, nonspecific palliative therapies are usually employed. These include emollients, counterirritants (menthol, phenol, camphor), anesthetics (pramoxine), or antiinflammatory agents (corticosteroids) applied topically. In addition to avoidance of irritants and systemic antipruritics, antihistamines or tranquilizers are usually added. For pruritis not associated with release of histamine, the nonsedating products are not beneficial. The majority of patients suffering from pruritis need systemic sedation to realize relief, which for obvious reasons adversely affects working people.

SUMMARY OF THE INVENTION

It has now been discovered that monocarboxylic acid esters and amides applied topically are an effective palliative treatment for pruritis, regardless of the etiology of the itching. In accordance with the invention, the monocarboxylic acid esters and amides are formulated and applied either alone or in combination with other antipruritic compounds, such as amine and "caine" anesthetics, ketones, alcohols, antihistamines, corticosteroids, tar, salicylic acid or counterirritants, or any combination of these agents.

DETAILED DESCRIPTION OF THE INVENTION AND PREFERRED EMBODIMENTS

The monocarboxylic acid esters and amides of the present invention are those derived from monocarboxylic acids of 5 to 19 carbon atom length, inclusive. The compounds include straight-chain and branched-chain species, and saturated and unsaturated species, including species with multiple unsaturation sites. Preferred are straight-chain aliphatic acids, either saturated or unsaturated, of 9 to 18 carbon atom length. Examples include pelargonic, capric, undecanoic, lauric, tridecanoic, myristic, myristoleic, palmitic, palmitoleic, hexandecanoic, oleic, linoleic, linolenic, and octadecanoic acids. The esters include glycerides and polyglycerides such as monoglycerides, triglycerides, hexaglycerides, and decaglycerides, as well as esters formed from methanol, ethanol, propylene glycol, polyethylene glycol and sorbitol, and saccharides such as sucrose. Specific examples of these esters include 1-monolaurin, 2-monolaurin, monocaprin, monomyristin, monolinolein; triglycerol caprylate, pelargonate, caprate, and laurate; hexaglycerol caproate, caprylate, pelargonate, caprate and laurate; decaglycerol butyrate, caprylate, pelargonate, caprate and laurate; and sucrose caprylate, caprate, laurate, myristate, palmitate, elaidate, oleate, and linoleate. Examples of amides are capratoyl-N,N-dimethylamide, lauryl-N,N-dimethylamide, myristoleyl-N,N-dimethylamide, and palmitoleyl-N,N-dimethylamide. A preferred example is lauryl-N,N-dimethylamide.

The compounds are generally applied in dermatological formulations. These include any of the various known mixtures and combinations which may be applied topically and will permit even spreading of the active ingredient over the affected area. Examples include creams, lotions, solutions, ointments, and unguents.

The concentration of the monocarboxylic acid ester or amide in the formulation is not critical and can vary over a wide range. The concentration may indeed range as high as the upper limit of dissolvability in any given formulation. The concentration should be a therapeutically effective concentration, however, and in most cases, best results are achieved within a range of about 0.5% to about 35% by weight, preferably from about 1% to about 11% by weight.

The formulation may contain additional ingredients on an optional basis, including both those which are biologically active and those which are biologically inactive. Examples of biologically active ingredients are amine- and "caine"-type local anesthetics, antihistamines, corticosteroids, alcohols and ketones, counterirritants and combinations of these agents. Specific examples within these groups include butamen, benzocaine, dibucaine, pramoxine, dimethisoquin, dyclonine, lidocaine, tetracaine, camphor, benzyl alcohol, menthol, phenol, phenolated sodium, resorcinol, tar, camphorated metacresol, diphenhydramine, tripelennamine, hydrocortisone, histamine, methyl nicotinate, capsicum, methyl salicylate, turpentine oil, allyl isothiocyanate, ammonia, and salicylic acid. The concentrations of these active ingredients can range from 0.025% to 60%, the most appropriate amounts in each case depending on the agent. Appropriate concentration ranges for any particular agent will be apparent to those skilled in the art.

Stratum corneum penetration enhancing compounds are usually included in dermatologic formulations to boost efficacy. Examples include propylene glycol, sodium lauryl sulfate, dimethylamide, N-methyl-2-pyrrolidone, and Azone (Nelson Research, Irvine, Calif.).

Examples of inactive ingredients are wetting agents, surfactants, emollients, and solvents.

The term "therapeutically effective amount" is used herein with reference to the amount of dermatological formulation to be applied in any particular case, and denotes any amount which will cause substantial relief of the pruritis when applied to the affected area repeatedly over a period of time. The amount will vary with the location of the affected area, the age and condition of the patient, the stage of advancement of the condition, and the type and concentration of formulation applied. Appropriate amounts in any given instance will be readily apparent to those skilled in the art or capable of determination by routine experimentation.

The compositions are generally applied in topical manner to the affected area, i.e., localized application to the skin region where the pruritis is manifest.

The following examples are offered for purposes of illustration, are intended neither to define nor limit the invention in any manner.

EXAMPLE 1

This example illustrates the preparation of the topical formulation in accordance with the present invention.

A therapeutic ointment was prepared by dissolving 15 grams of 1-monolaurin (obtained from Lauricidin, Inc., Okemos, Mich.) in 9 mL of commercial isopropyl alcohol heated to 50° C. Commercial propylene glycol (7 mL) was then incorporated into the solution and the resulting mixture was cooled overnight at 24° C. The mixture was then worked into 100 g of Aquaphor (4-chloro-5-sulfamoyl-2',6'-salicyloxylidide, obtained from Beiersdorf, Inc., Norwalk, Conn.) on a pill tile.

EXAMPLE 2

An 86-year old woman with a five-year history of intractable pruritis without underlying cutaneous or systemic disease applied the formulation of Example 1 topically to the affected areas three times daily. She experienced complete resolution of the itching within seven days.

EXAMPLE 3

Ten patients suffering from pruritic psoriasis vulgaris that had failed all standard topical and systemic treatments were treated twice daily with the formulation of Example 1. All of these patients experienced complete resolution of pruritis within ten days, even though the psoriatic lesions had not completely cleared.

The foregoing description is offered primarily for purposes of illustration. It will be readily apparent to those skilled in the art and numerous variations in both the formulations and their method of use, not mentioned above, may be made without departing from the spirit and scope of the invention.

What is claimed is:

1. A method for the treatment of a subject suffering from a disease condition that manifests pruritis, said method comprising administering to said subject a therapeutically effective amount of a dermatological formulation comprising from about 0.5% to about 35% by weight of a compound selected from a group consisting of esters and amides of monocarboxylic acids, said monocarboxylic acids having 5 to 19 carbon atoms, said esters being selected from the group consisting of glycerides, saccharides, and esters of methanol, ethanol, propylene glycol, and polyethylene glycol, and said amides being N,N-dimethylamides.

2. A method for the treatment of a subject suffering from psychogenic or senile pruritis, said method comprising administering to said subject a therapeutically effective amount of a dermatological formulation comprising from about 0.5% to about 35% by weight of a compound selected from a group consisting of esters and amides of monocarboxylic acids, said monocarboxylic acids having 5 to 19 carbon atoms, said esters being selected from the group consisting of glycerides, saccharides, and esters of methanol, ethanol, propylene glycol, and polyethylene glycol, and said amides being N,N-dimethylamides.

3. A method in accordance with claim 1 in which said formulation further comprises one or more members selected from the group consisting of amine and caine anesthetics, ketones, alcohols, antihistamines, corticosteriods, counterirritants, tars, and salicylic acid.

4. A method in accordance with claim 1 in which said formulation further comprises one or more members selected from the group consisting of butamen, benzocaine, dibucaine, dimethisoquin, dyclonine, lidocaine, tetracaine, camphor, benzyl alcohol, menthol, pramoxine, phenol, phenolated sodium, resorcinol, tar, camphorated metacresol, diphenhydramine, tripelennamine, hydrocortisone, histamine, methyl nicotinate, capsicum, methyl salicylate, turpentine oil, allyl isothiocyanate, ammonia, and salicylic acid.

5. A method in accordance with claim 1 in which said dermatological formulation comprises from about 1% to about 11% by weight of said compound.

6. A method in accordance with claim 1 in which said monocarboxylic acids are straight-chain monocarboxylic acids 9 to 18 carbon atoms in length.

7. A method in accordance with claims 1, 2, 3, 4, 5, or 6 in which said compound is an ester selected from the group consisting of glycerides, saccharides, and esters of methanol, ethanol, propylene glycol, and polyethylene glycol.

8. A method in accordance with claims 1, 2, 3, 4, 5, or 6 in which said compound is an ester selected from the group consisting of monoglycerides, triglycerides, hexaglycerides, decaglycerides and sucrose esters.

9. A method in accordance with claims 1, 2, 3, 4, 5, or 6 in which said compound is selected from the group consisting of 1-monolaurin, 2-monolaurin, monocaprin, monomyristin, monolinolein, triglycerol caprylate, triglycerol pelargonate, triglycerol caprate, triglycerol laurate, hexaglycerol caproate, hexaglycerol caprylate, hexaglycerol pelargonate, hexaglycerol caprate, hexaglycerol laurate, decaglycerol butyrate, decaglycerol caprylate, decaglycerol pelargonate, decaglycerol caprate, decaglycerol laurate, sucrose myristate, sucrose palmitate, sucrose elaidate, sucrose oleate, and sucrose linoleate.

10. A method in accordance with claims 1, 2, 3, 4, 5, or 6 in which said compound is 1-monolaurin.

11. A method in accordance with claims 1, 2, 3, 4, 5, or 6 in which said compound is an amide selected from the group consisting of capratoyl-N,N-dimethylamide, lauryl-N,N-dimethylamide, myristoleyl-N,N-dimethylamide, palmitoleyl-N,N-dimethylamide, linoleyl-N,N-dimethylamide, and octadecanoyl-N,N-dimethylamide.

12. A method in accordance with claims 1, 2, 3, 4, 5, or 6 in which said compound is lauryl-N,N-dimethylamide.

13. A method in accordance with claims 1, 2, 3, 4, 5, or 6 in which said dermatological formulation further includes a stratum corneum penetration enhancer.

* * * * *